(12) United States Patent
Taal et al.

(10) Patent No.: US 9,655,942 B2
(45) Date of Patent: May 23, 2017

(54) MEDICAL FORMULATION FOR TREATING HYPERCHOLESTEROLEMIA

(71) Applicants: Leendert Taal, Hengelo (NL); Anita Monique Taal-Vlas, Hengelo (NL)

(72) Inventors: Leendert Taal, Hengelo (NL); Anita Monique Taal-Vlas, Hengelo (NL)

(*) Notice: Subject to any disclaimer, the term of this patent is extended or adjusted under 35 U.S.C. 154(b) by 0 days.

(21) Appl. No.: 14/654,270

(22) PCT Filed: Dec. 24, 2013

(86) PCT No.: PCT/NL2013/050951
§ 371 (c)(1),
(2) Date: Jun. 19, 2015

(87) PCT Pub. No.: WO2014/104884
PCT Pub. Date: Jul. 3, 2014

(65) Prior Publication Data
US 2015/0328276 A1    Nov. 19, 2015

(30) Foreign Application Priority Data
Dec. 27, 2012   (NL) .................................... 2010065

(51) Int. Cl.
| | | |
|---|---|---|
| *A61K 36/899* | (2006.01) | |
| *A61K 31/122* | (2006.01) | |
| *A61K 31/455* | (2006.01) | |
| *A61K 31/355* | (2006.01) | |
| *A61K 31/202* | (2006.01) | |
| *A61K 31/716* | (2006.01) | |
| *A61K 31/045* | (2006.01) | |
| *A61K 31/315* | (2006.01) | |
| *A61K 9/48* | (2006.01) | |
| *A61K 36/82* | (2006.01) | |
| *A61K 35/60* | (2006.01) | |
| *A61K 36/062* | (2006.01) | |
| *A61K 36/15* | (2006.01) | |
| *A61K 36/288* | (2006.01) | |
| *A61K 36/54* | (2006.01) | |

(52) U.S. Cl.
CPC .......... *A61K 36/899* (2013.01); *A61K 9/4825* (2013.01); *A61K 31/045* (2013.01); *A61K 31/122* (2013.01); *A61K 31/202* (2013.01); *A61K 31/315* (2013.01); *A61K 31/355* (2013.01); *A61K 31/455* (2013.01); *A61K 31/716* (2013.01); *A61K 35/60* (2013.01); *A61K 36/062* (2013.01); *A61K 36/15* (2013.01); *A61K 36/288* (2013.01); *A61K 36/54* (2013.01); *A61K 36/82* (2013.01)

(58) Field of Classification Search
None
See application file for complete search history.

(56) References Cited

U.S. PATENT DOCUMENTS

| | | | |
|---|---|---|---|
| 6,436,406 B1 | 8/2002 | Yegorova | |
| 8,114,445 B2 * | 2/2012 | Hastings | ................. A23L 1/293 424/725 |
| 2010/0136104 A1 | 6/2010 | Squashic et al. | |

FOREIGN PATENT DOCUMENTS

| | | |
|---|---|---|
| FR | 2936711 A1 | 4/2010 |
| WO | WO0176382 A1 | 10/2001 |
| WO | WO2012137163 A1 | 10/2012 |

OTHER PUBLICATIONS

Asset et al., Effects of dietary maritime pine (*Pinus pinaster*)-seed oil on high-density lipoprotein levels and in vitro cholesterol efflux in mice expressing human apolipoprotein A-I, Br J Nutr (2000), 84(3):353-360.
Choi et al., Hypolipidemic and Antioxidant Effects of Dandelion (*Taraxacum officinale*) Root and Leaf on Cholesterol-Fed Rabbits, Int J Mol Sci (2010), 11(1):67-78.
Jones et al., Phytosterols as functional food ingredients: linkages to cardiovascular disease and cancer, Curr Opin Clin Nutr Metab Care (2009), 12(2):147-151.
Ranasinghe et al., Effects of Cinnamomum zeylanicum (Ceylon cinnamon) on blood glucose and lipids in a diabetic and healthy rat model, Pharmacognosy Res (2012), 4(2):73-79.
Database TCM, Chen Yuande: "A new type edible sugar for health promotion", XP002720056, Database accession No. CN-98121892-A abstract & CN 1 223 806 A, Jul. 28, 1999.
Database WPI, Week 200657, Thomson Scientific, London, GB; AN 2006-554162, XP002720057, & JP 2006 206472 A (Ogawa Koryo KK) Aug. 10, 2006, abstract.
Database WPI, Week 200842, Thomson Scientific, London, GB; AN 2008-G63336, XP002720055, & JP 2008 125485 A (IB Kashohin KK) Jun. 5, 2008, abstract.

* cited by examiner

*Primary Examiner* — Susan Hoffman
(74) *Attorney, Agent, or Firm* — Rudy J. Ng; Bret E. Field; Bozicevic, Field & Francis LLP

(57) ABSTRACT

The present invention relates to a medical formulation comprising: cinnamomum zeylanicum; Pinus pinaster; extract of a plant belonging to the Saccharum genus; Monascus purpureus; Taraxacum officinale; Camellia sinensis; vitamin B3; alpha tocopherol; coenzyme $Q_{10}$; fish oil comprising eicosapentaenoic acid and docosahexanoic acid; beta-glucan; and/or cholecalciferol. The invention also relates to the medical formulation as a medicament, and especially for treating hypercholesterolemia.

15 Claims, 7 Drawing Sheets

MEDICAL FORMULATION FOR TREATING HYPERCHOLESTEROLEMIA

The present invention relates to medical formulations for preventing and/or treating hypercholesterolemia levels in a patient, and the use thereof for treating hypercholesterolemia.

Hypercholesterolemia is known as the presence of high levels of cholesterol in the blood. Hypercholesterolemia is typically due to a combination of genetically and environmental factors. Examples of environmental factors are obesity and diet. Further, hypercholesterolemia may be the result of secondary causes such as diabetes mellitus type 2, tobacco and alcohol use, stress and anorexia nervosa.

Diet has a substantial effect on blood cholesterol levels. Especially fat intake of saturated fats contributes to blood cholesterol levels.

Cholesterol, as being insoluble in water, is transported in the blood plasma within lipoproteins. These lipoproteins can be further subdivided in, amongst others, low density lipoprotein (LDL) and high density lipoprotein (HDL). High density lipoprotein (HDL) is informally dsignated as 'good cholesterol' whereas low density lipoprotein (LDL) is informally designated as 'bad cholesterol'. It is understood that high density cholesterol (HDL) has an important role in reducing the low density cholesterol (LDL) levels, as high density cholesterol (HDL) is able to remove cholesterol from the artery and transport it to the liver for excretion.

An increased blood level of low density lipoprotein (LDL) is associated with an increased risk of atherosclerosis and cardiovascular disease. Low density lipoprotein (LDL) contributes to deterioration of the vessel wall conditions, and may eventually lead to the formation of plaques in arteries. Thrombosis is also mentioned in association with high low density lipoprotein (LDL) levels.

Due to the increasing amount of individuals suffering from hypercholesterolemia, there are numerous efforts known to reduce blood cholesterol levels. Besides life style changes, statins are commonly used as medicines.

Statins may lower total blood cholesterol levels by inhibiting the HMG-CoA reductase enzyme, which plays a central role in the production of cholesterol by the liver. By lowering total blood cholesterol levels, the use of statins also reduce the blood levels of high density lipoprotein (HDL), which is negative due to beneficial properties of high density lipoprotein (HDL) such as transportation from cholesterol within artery back to the liver for excretion. Further, the use of statins does not contribute to the decrease of triglycerides, while high blood levels of triglycerides is also associated with atherosclerosis.

Further, the use of statins may lead to negative side effects such as muscle pain and raised liver enzymes. Gastrointestinal problems related to the use of statins are also reported. Further, problems are reported related to the impotence of men by using statins. As a result of the side effects, the therapy loyalty of statin users is remarkably low. It is known from studies that 74.5% of individuals having a statin prescription has not taken the medicament within the first 12 weeks after the prescription. Of this group, 53.4% has not taken the statins because they were afraid for side effects. Given the substantial health care costs for hypercholesterolemia, the above low therapy loyalty constitutes an important drawback in the current therapies for treating hypercholesterolemia.

Accordingly, although, beneficial effects on cholesterol blood levels have been reported for statins, there remains a need in the art for other medical formulations for the treatment of hypercholesterolemia.

Therefore, an object of the present invention is to provide new medical formulations for the treatment of hypercholesterolemia, and especially for lowering the blood levels of low density lipoprotein (LDL).

According to the present invention, this object, amongst other objects, is met by providing new medical formulations for the treatment of hypercholesterolemia, and especially for lowering the blood levels of low density lipoprotein (LDL).

This object, amongst other objects, is met by the medical formulation according to the appended claim 1.

Specifically, this object is met by providing a medical formulation comprising, as active ingredients:
cinnamomum zeylanicum;
Pinus pinaster;
extract of a plant belonging to the Saccharum genus;
Monascus purpureus;
Taraxacum officinale;
Camellia sinensis;
vitamin B3;
alpha tocopherol;
coenzyme $Q_{10}$;
fish oil comprising eicosapentaenoic acid and docosahexanoic acid;
beta-glucan; and/or
cholecalciferol.

Surprisingly, it was found by the present inventors that the present medical formulation provides a synergistic effect in individuals suffering from hypercholesterolemia. Specifically was found that the present medical formulations are able to lower the blood levels of low density lipoprotein (LDL), while the blood levels of high density lipoprotein (HDL) remain intact, or even increase. Further, is noticed that by using the present medical formulation, the triglycerides blood level are reduced. Further, the present inventors found that by using the present medical formulation, the condition of blood vessel walls improve significantly, thereby reducing the risk of associated diseases such as atherosclerosis. Further, the present inventors found that the micro circulation in the capillary system improves when the present medical formulation is used for three weeks. During the tests the individuals taking the present medical formulation did not perceive negative side effects of the medicament. Therefore, the present medical formulation can advantageously be used for preventing vessel wall associated diseases such as atherosclerosis, thrombosis and cardiovascular disease.

In a preferred embodiment, the present medical formulation further comprises zinc bisglycinate and/or keratin hypericum.

In a preferred embodiment of the present invention, the present medical formulation comprises:
bark extract of cinnamomum zeylanicum;
fibre extract of Pinus pinaster;
bark extract of a plant belonging to the Saccharum genus;
extract of Monascus purpureus;
leave extract of Taraxacum officinale;
leave extract of Camellia sinensis;
vitamin B3;
alpha tocopherol;
coenzyme $Q_{10}$;
fish oil comprising 15 to 25 wt % of the fish oil eicosapentaenoic acid and 7 to 15 wt % of the fish oil docosahexanoic acid;
beta-glucan;
cholecalciferol and/or
zinc bisglycinate.

It was found that by using the present medical formulation the systolic blood pressure was significantly reduced after 3 months administration. This is advantageous because the reduced blood pressure indicates that the viscosity of the blood was increased, which lowers the risk of infarction.

According to a further preferred embodiment, the present medical formulations comprise, as daily dose:
- 1 to 500 mg bark extract of *cinnamomum zeylanicum*;
- 1 to 300 mg fibre extract of *Pinus pinaster*;
- 1 to 300 mg bark extract of a plant belonging to the *Saccharum* genus;
- 100 to 1500 mg extract of *Monascus purpureus*;
- 1 to 300 mg leave extract of *Taraxacum officinale*;
- 1 to 300 mg leave extract of *Camellia sinensis*;
- 1 to 300 mg vitamin B3;
- 1 to 300 mg alpha tocopherol 50%;
- 1 to 400 mg coenzyme $Q_{10}$;
- 1 to 500 mg fish oil comprising 18 to 22 wt % of the fish oil eicosapentaenoic acid and 10 to 15 wt % of the fish oil docosahexanoic acid;
- 0.1 to 100 mg beta-glucan; and/or
- 0.1 to 200 mg cholecalciferol. Preferably the present medical formulation further comprises 1 to 100 mg zinc bisglycinate.

According to a further preferred embodiment, the present medical formulations comprise, as daily dose:
- 1 to 250, preferably 1 to 50 mg bark extract of *cinnamomum zeylanicum*;
- 1 to 150, preferably 1 to 50 mg fibre extract of *Pinus pinaster*;
- 1 or 10 to 150, preferably 1 to 50 mg bark extract of a plant belonging to the *Saccharum* genus;
- 1 or 250 to 500 mg extract of *Monascus purpureus*, or preferably 1 to 50 or 1 to 25 mg lovastatin;
- 1 to 150, preferably 0.5 to 50 mg leave extract of *Taraxacum officinale*;
- 0.5 or 1 to 50 mg leave extract of *Camellia sinensis*;
- 1 or 5 to 50 or to 100 mg vitamin B3;
- 1 or 5 to 20 or 100 mg 50% alpha tocopherol;
- 10 to 250, preferably 10 to 150 mg coenzyme $Q_{10}$;
- 1 to 150 mg fish oil comprising 18 to 22 wt % of the fish oil eicosapentaenoic acid and 10 to 15 wt % of the fish oil docosahexanoic acid;
- 0.5 to 20 or to 100 mg beta-glucan;
- 0.5 to 20 mg cholecalciferol or vitamin $D_3$; and/or
- 1 to 50 mg zinc bisglycinate.

'*Cinnamomum zeylanicum*' as used in the present context is derived from cinnamon from Sri Lanka, such as *Cinnamomum verum*.

'*Pinus pinaster*', or maritime Pine is a pine originating from the Mediterranean region. Extracts can suitably be made from leaves or bark. Preferably, the present extract is pycnogenol.

'*Monascus purpureus*' is a fungus used in the production of fermented food. It is believed that the fungus produces the natural statin lovastatin. The present invention preferably comprises lovastatin originating from *Monascus purpureus*.

'*Taraxacum officinale*' or common dandelion is an abundantly growing weed in temperate regions of the world. The flowers of the plant are used to produce wine. The plant and leaves are suitable to provide extracts having the synergetic use in the present medical formulation.

The present 'bark extract of a plant belonging to the *Saccharum* genus' is preferably policosanol, or polycosanol derived from sugar cane.

'*Camellia sinensis*' or tea plant, originates from Southeast Asia and is usually used to make tea. Preferably, the leaves of 'Tea sinensins' are used, more preferably the leaves of plants to produce green tea. Green tea is advantageous due to its natural anti oxidants.

'Beta-glucan' as used in the present context means polysaccharides containing only glucose, preferably D glucose, as structural components which are linked by beta glycosidic bonds. The present beta-glucan is preferably, beta-1,2,3-glucan, beta-1,3-glucan (or beta-1,3, or 1,4-D-glucan) and/or beta-1,6-glucan, more preferably a combination of beta-1,3-glucan and beta 1,6-D-glucan.

Alpha tocopherol as used in the present context means vitamin E, preferably having as active ingredient (2R)-2,5,7,8-Tetramethyl-2-[(4R,8R)-(4,8,12-trimethyltridecyl)]-6-chromanol.

Cholecalciferol as used in the present context is a form of vitamin D, which is also known as vitamin D3.

The ingredients of the present invention can be extracted from the natural sources by known extraction techniques in the art. Further, common ingredients such as for example fish oil and/or coenzyme Q10 may be commercially available.

Preferably, the present vitamin B3 is nicotinamide, i.e. the amide of nicotinic acid, also known as pyridine-3-carboxamide.

According to yet another preferred embodiment, the present medical formulation further comprises micronutrients and/or trace elements.

According to another preferred embodiment, the present medical formulations comprise pharmaceutically acceptable carriers and excipients.

According to another preferred embodiment, the present medical formulations are formulated for oral administration, preferably in capsules comprising or consisting of gelatin. This is advantageous since gelatin capsules do not comprise animal derived ingredients, such as pig derived ingredients, thereby avoiding possible religious problems by the individuals using said capsule. Alternatively, the present medical formulation may be suitable for intravenous, subcutaneous and/or intraperitoneal administration.

The medical formulations according to the present invention may be administered in standard manner for the disease condition that it is desired to treat, for example by oral, topical, parenteral, buccal, nasal, vaginal or rectal administration or by inhalation or insufflation. Preferred however is oral administration.

For these purposes, the compounds according to the present invention may be formulated by means known in the art into the form of, for example, tablets, pellets, capsules, aqueous or oily solutions, suspensions, emulsions, creams, ointments, gels, nasal sprays, suppositories, finely divided powders or aerosols or nebulizers for inhalation, and for parenteral use (including intravenous, intramuscular or infusion) sterile aqueous or oily solutions or suspensions or sterile emulsions.

However, preferred are capsules such as soft or hard gelatine capsules.

The formulations according to the present invention can also comprise carriers and additives which are commonly used in the pharmaceutical field. Such carriers and additives can for example be:

Solvents such as purified water, water for injection, physiological saline, peanut oil, ethanol, and glycerin;

Carriers such as starch, lactose, glucose, sucrose, microcrystalline cellulose, methyl cellulose, calcium sulfate, calcium carbonate, talc, titanium oxide, trehalose, and xylitol;

Coating agents such as sucrose, gelatin, and cellulose acetate phthalate; basis: vaseline, vegetable oil, macrogol, oil in water type emulsion base, water in oil type emulsion base;

Binders such as starch and derivatives thereof, cellulose and derivatives thereof, naturally-occurring high molecular compounds such as gelatin, sodium alginate, tragacanth, acacia and the like, synthetic high molecular compounds such as polyvinyl pyrrolidone, dextrin, and hydroxypropyl starch;

Lubricants such as stearic acid and salts thereof, talc, wax, wheat starch, macrogol, hydrogenated vegetable oil, sucrose fatty acid ester, and polyethylene glycol;

Disintegrants such as starch and derivatives thereof, gelatin, gelatin powder, sodium bicarbonate, cellulose and derivatives thereof, calcium carmellose, hydroxypropyl starch, carboxymethyl cellulose and salts and cross-linked materials thereof, and low-substituted types of hydroxypropyl cellulose;

Solution adjuvants such as cyclodextrin, ethanol, propylene glycol, and polyethylene glycol; suspending agents such as acacia, tragacanth, sodium alginate, aluminum monostearate, citric acid, and various surfactants;

Viscosity-increasing agents such as sodium carmellose, polyvinyl pyrrolidone, methyl cellulose, hydroxypropylmethyl cellulose, polyvinyl alcohol, tragacanth, acacia, and sodium alginate;

Emulsifying agents such as acacia, cholesterol, tragacanth, methyl cellulose, various surfactants, lecithin;

Stabilizers such as sodium hydrogensulfite, ascorbic acid, tocopherol, chelating agent, inert gas, and reducing substance;

Buffers such as sodium hydrogenphosphate, sodium acetate, and boric acid;

Tonicity agents such as sodium chloride and glucose;

Soothing agents such as procaine hydrochloride, lidocaine, benzyl alcohol;

Preservatives such as benzoic acid and salts thereof, para-oxybenzoic acid esters, chlorobutanol, invert soap, benzyl alcohol, phenol, and thimerosal; flavoring agents such as sucrose, saccharin, *glycyrrhiza* extract, sorbitol, xylitol, and glycerin;

Given the beneficial properties of the present medical formulations, the present invention relates, according to another aspect, to the present medical formulations for use as a medicament, preferably for humans.

In a preferred embodiment, the present invention relates to the present medical formulations for preventing/treating a disease selected from the group consisting of hypercholesterolemia, atherosclerosis, stroke, hypertension, diabetes mellitus and coronary heart disease.

Especially, the present invention relates to the present medical formulations for recuperation of vascular walls, lowering low density lipoprotein blood levels, lowering the viscosity of blood, lowering blood pressure, and/or increasing high density lipoprotein levels. Preferably, the present invention relates to the present medical formulation for reducing the risk factor in humans, or patients, at risk of hypercholesterolemia, wherein the risk factor is determined by the total cholesterol blood level divided by the HDL blood level.

In a preferred embodiment, the present invention relates to the present medical formulation for treating a disease, wherein the medical formulation is administered orally twice a day, preferably during breakfast and during dinner, preferably for a time period of 1 to 6 months, more preferably for a time period of about 3 or about 4 months.

In a preferred embodiment, the present invention relates to the present medical formulation for lowering LDL cholesterol blood levels, for improving total cholesterol blood levels, for increasing HDL cholesterol blood levels, for lowering triglyceride blood levels and/or for lowering the systolic blood pressure, preferably in individuals at risk of hypercholesterolemia.

According to yet another aspect, the present invention relates to a method for preventing/treating a disease selected from the group consisting of hypercholesterolemia, atherosclerosis, stroke, hypertension, diabetes mellitus and coronary heart disease, comprising administering the present medical formulations.

The invention is further elucidated in the examples below, in which reference is made to the figures. Wherein.

Figure 1A:
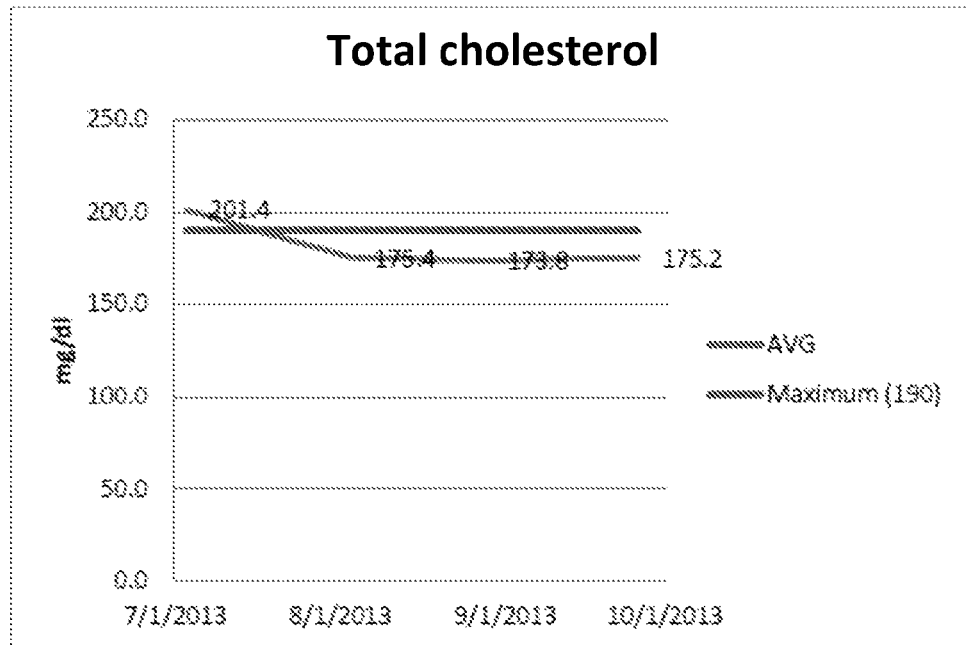
FIG. 1 shows total cholesterol levels in mg/dl during a period of 3 months (FIG. 1*a* control group 2, FIG. 1*b* experimental group 2)

Although the invention has been described in some detail above by referring to specific preferred embodiments, it should be understood that the scope of the present invention, which solely defined by the appended claims, is not limited to these embodiments. The skilled person will appreciate that modifications and adaptations can be made to the present invention without deviating from the inventive concept of the invention.

Example 1

Blood Level Effects of Present Medical Formulation 5 patients suffering from increased low density lipoprotein (LDL) levels were treated for three weeks with a formulation comprising, as daily dose:

70 mg bark extract of *cinnamomum zeylanicum;*
45 mg fibre extract of *Pinus pinaster;*
45 mg bark extract of a plant belonging to the *Saccharum* genus;
700 mg extract of *Monascus purpureus;*
50 mg leave extract of *Taraxacum officinale;*
100 mg leave extract of *Camellia sinensis;*
20 mg vitamin B3;
20 mg 50% alpha tocopherol;
100 mg coenzyme $Q_{10}$;
155 mg fish oil comprising 19.2 wt % eicosapentaenoic acid and 12.9 wt % docosahexanoic acid;
1 mg beta-glucan; and
1 mg cholecalciferol.

The above ingredients were divided in two capsules for daily intake. The capsules were composed of gelatin. One capsule was taken during breakfast; the other was taken during dinner.

Results

|  | Parameter (in mg/dl) | T = 0 | After 3 weeks |
|---|---|---|---|
| Patient no 1. | Cholesterol | 269 | 272 |
|  | Triglyceride | 135 | 138 |
|  | HDL cholesterol | 59 | 59 |
|  | LDL cholesterol | 195 | 102 |
| Patient no. 2 | Cholesterol | 271 | 278 |
|  | Triglyceride | 131 | 132 |
|  | HDL cholesterol | 57 | 58 |
|  | LDL cholesterol | 152 | 104 |
| Patient no. 3 | Cholesterol | 268 | 270 |
|  | Triglyceride | 129 | 130 |
|  | HDL cholesterol | 55 | 59 |
|  | LDL cholesterol | 164 | 120 |
| Patient no. 4 | Cholesterol | 264 | 268 |
|  | Triglyceride | 132 | 134 |
|  | HDL cholesterol | 59 | 61 |
|  | LDL cholesterol | 132 | 108 |

|  | Parameter | T = 0 | After 3 weeks |
|---|---|---|---|
| Patient no. 5 | Cholesterol (mmol/L) | 6.03 | 3.8 |
|  | Triglyceride (mmol/L) | 2.6 | 1.6 |
|  | HDL cholesterol (mmol/L) | 1.17 | 1.23 |
|  | LDL cholesterol (mg/dl) | 471 | 269 |

DISCUSSION

The above results clearly indicate that after three weeks the blood level of LDL cholesterol reduced significantly, to levels which is within the recommended range of <130 mg/dl. Further, the above results show that the HDL cholesterol blood level is not reduced, and even increased somewhat. Thus, by using the above medical formulation, the LDL blood cholesterol levels are reduced while the HDL blood cholesterol levels are not reduced.

Example 2

Blood Level Effects of Present Medical Formulation

As control, group 1 of 5 patients suffering from increased low density lipoprotein (LDL) levels were treated for three months with a formulation comprising, as daily dose 11.40 mg extract of lovastatin.

A group 2 of 14 patients suffering from increased low density lipoprotein (LDL) levels were treated for three months with a formulation comprising, as daily dose:
- 4.80 mg bark extract of *cinnamomum zeylanicum;*
- 24.20 mg fibre extract of *Pinus pinaster;*
- 24.00 mg bark extract *Saccharum officinarum;*
- 11.40 mg lovastatin;
- 1.2 mg leave extract of *Taraxacum officinale;*
- 16 mg leave extract of *Camellia sinensis;*
- 20 mg nicotinamide;
- 14 mg 50% alpha tocopherol;
- 60 mg coenzyme $Q_{10}$;
- 37.80 mg fish oil comprising 19.2 wt % eicosapentaenoic acid and 12.9 wt % docosahexanoic acid;
- 60.00 mg beta-glucan; and
- 1 mg cholecalciferol.

The above ingredients were divided in two capsules for daily intake. The capsules were composed of gelatin. One capsule was taken during breakfast; the other was taken during dinner.

Results

TABLE 1

|  | Group 1 | | | Group 2 | | |
|---|---|---|---|---|---|---|
|  | T = 0 | T = 3 | Δ | T = 0 | T = 3 | Δ |
| Total cholesterol (mg/dl) | 201.4 | 175.2 | −26.2 | 237.6 | 199.9 | −37.7 |
| HDL (mg/dl) | 72.0 | 68.0 | −4.0 | 60.2 | 65.6 | 5.4 |
| LDL (mg/dl) | 96.2 | 73.2 | −23.0 | 144.0 | 99.5 | −44.5 |
| Non-HDL cholesterol (mg/dl) | 129.4 | 101.4 | −28.0 | 177.5 | 134.4 | −43.1 |
| Risk factor (mg/dl) | 2.91 | 2.50 | −0.41 | 4.18 | 3.19 | −0.99 |
| Triglycerides (mg/dl) | 165.8 | 146.8 | −19 | 170.5 | 142.8 | −27.7 |
| Systolic (mmHg) | 120.0 | 130.0 | 10 | 164.3 | 128.8 | −35.5 |
| Diastolic (mmHg) | 79.2 | 79.1 | −0.1 | 85.8 | 76.1 | −9.7 |

Figure 1B:
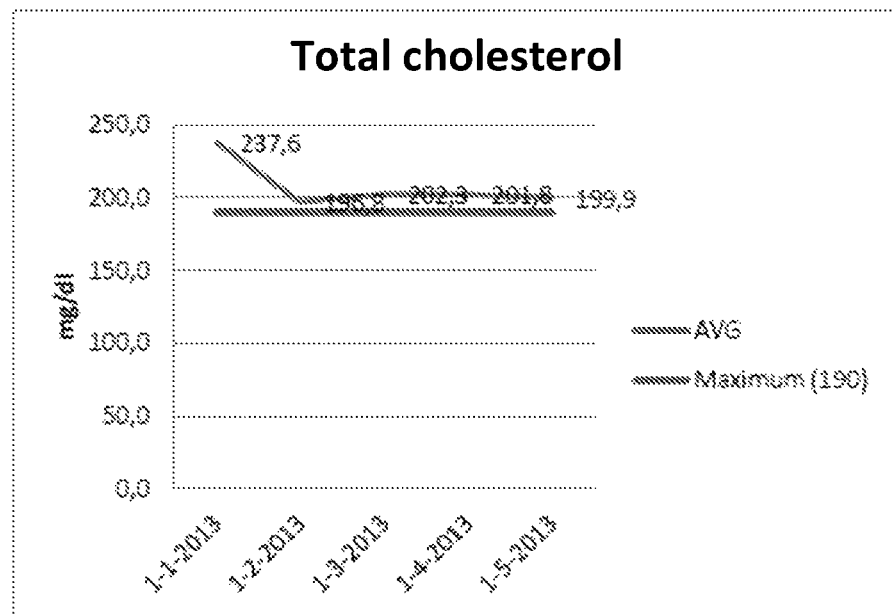
Figure 2A:
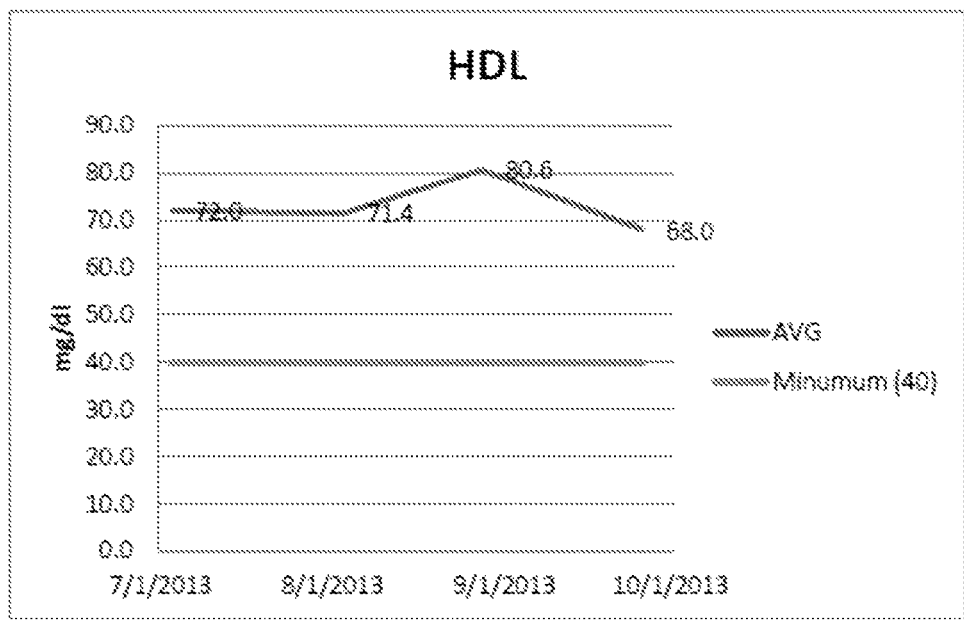
FIG. 2 shows the HDL levels in mg/dl during a period of 3 months (FIG. 2*a* control group 2, FIG. 2*b* experimental group 2)
Figure 2B:
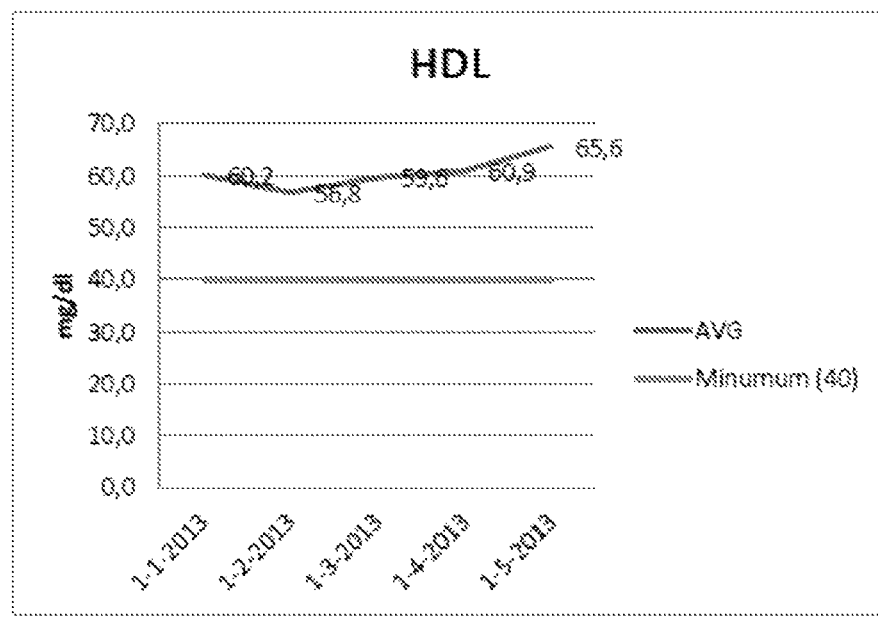
Figure 3A:
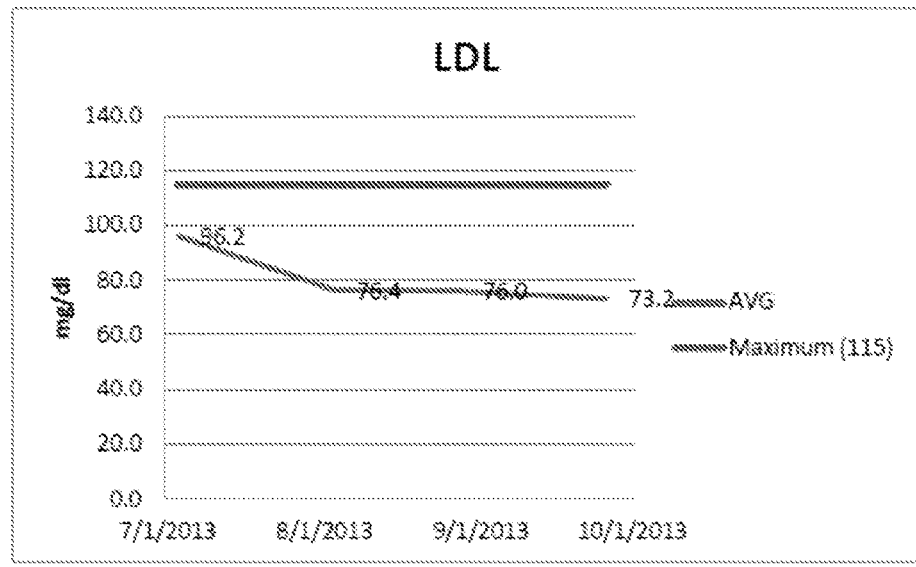
FIG. 3 shows the LDL levels in mg/dl during a period of 3 months (FIG. 3*a* control group 2, FIG. 3*b* experimental group 2)
Figure 3B:
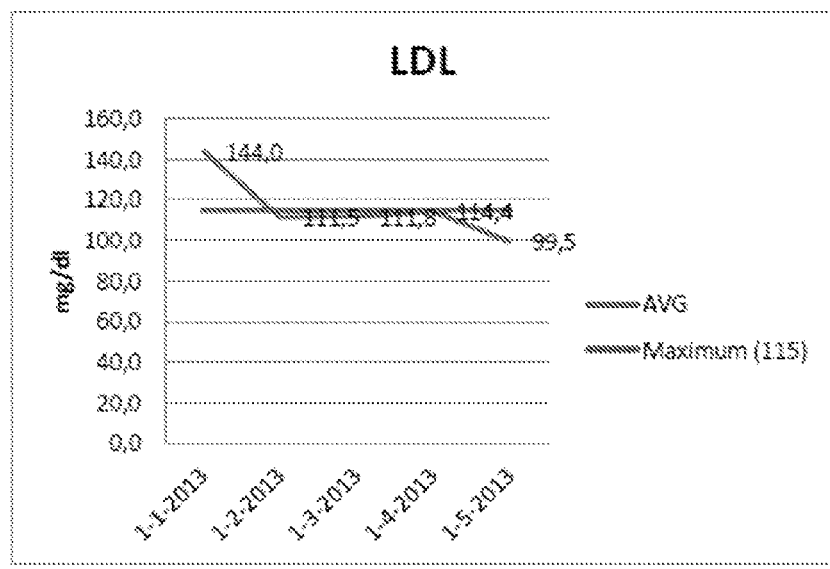
Figure 4A:
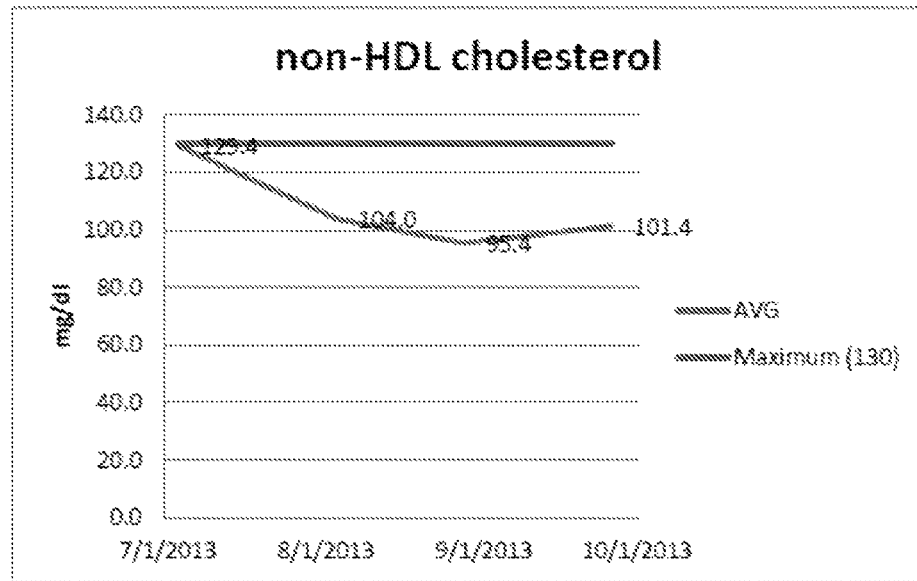
FIG. 4 shows the non-HDL levels in mg/dl during a period of 3 months (FIG. 4*a* control group 2, FIG. 4*b* experimental group 2)
Figure 4B:
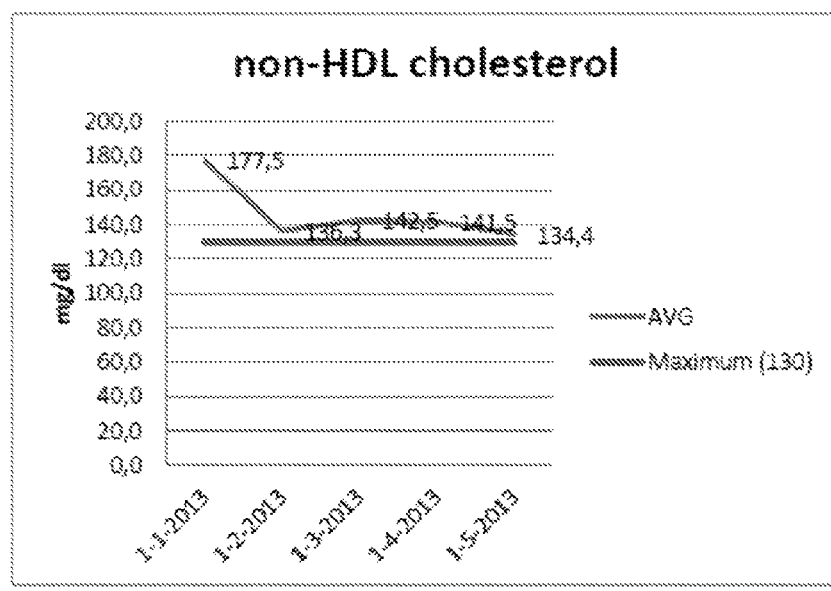
Figure 5A:
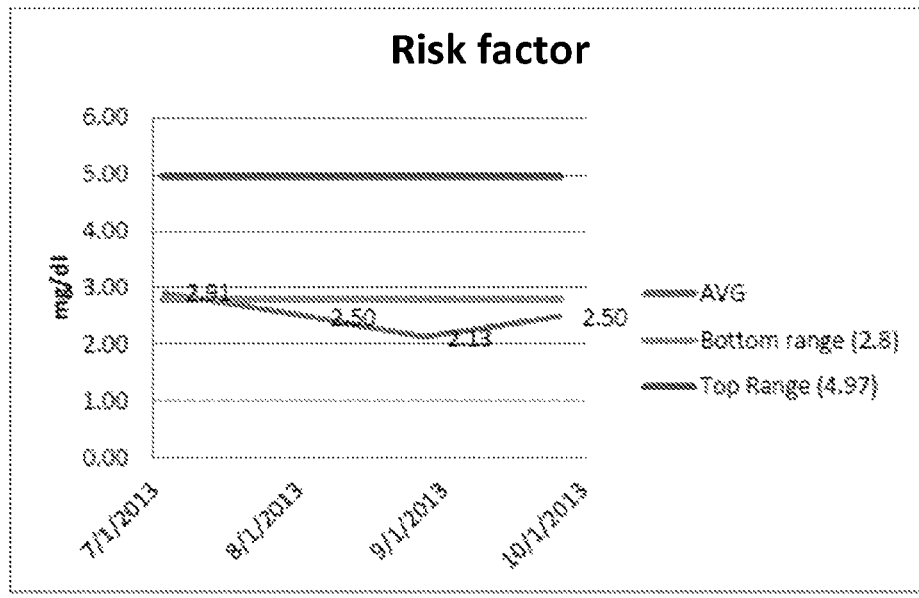
FIG. 5 shows the risk factor during a period of 3 months (FIG. 5*a* control group 2, FIG. 5*b* experimental group 2)
Figure 5B:
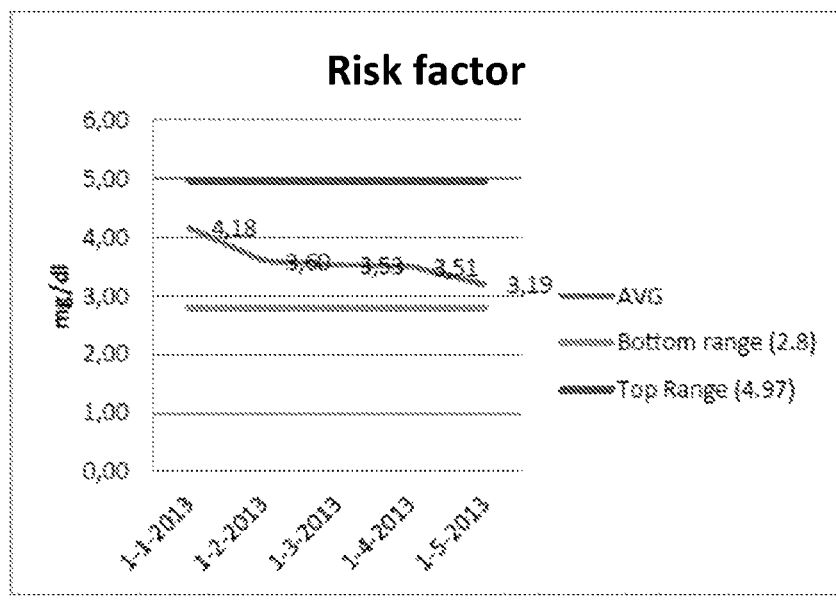
Figure 6A:
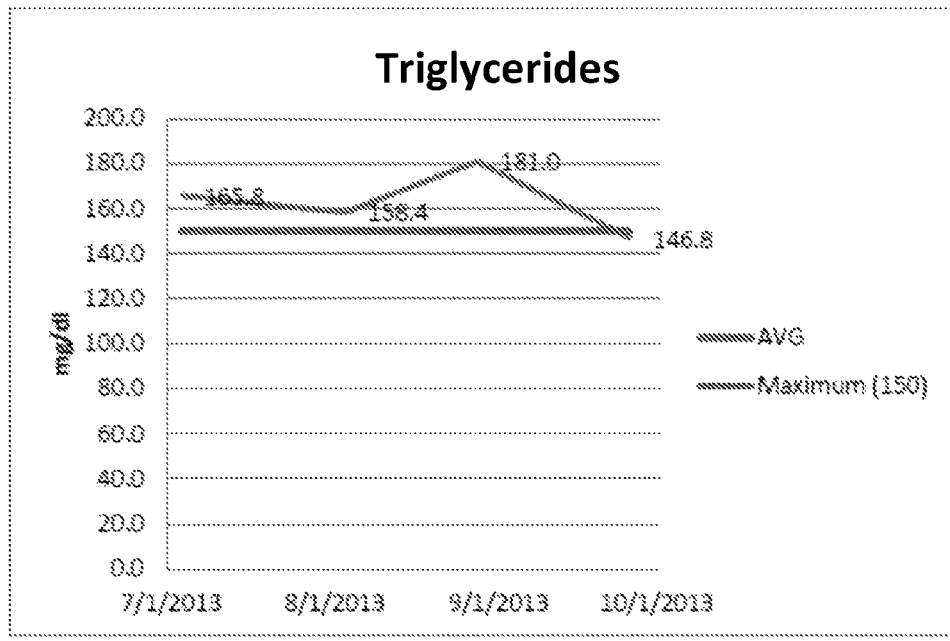
FIG. 6 shows the triglyceride levels in mg/dl during a period of 3 months (FIG. 6*a* control group 2, FIG. 6*b* experimental group 2)
Figure 6B:
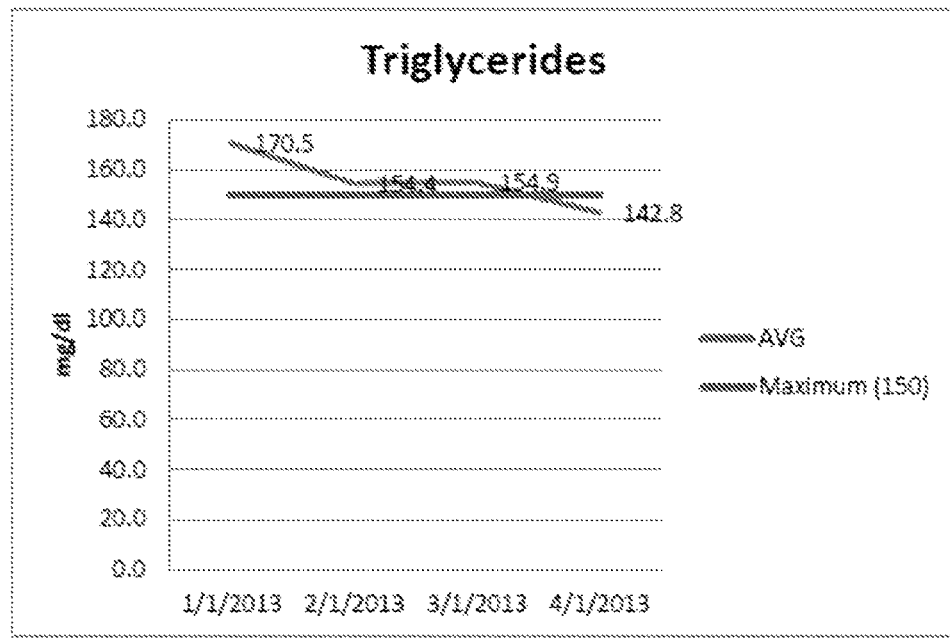
Figure 7A:
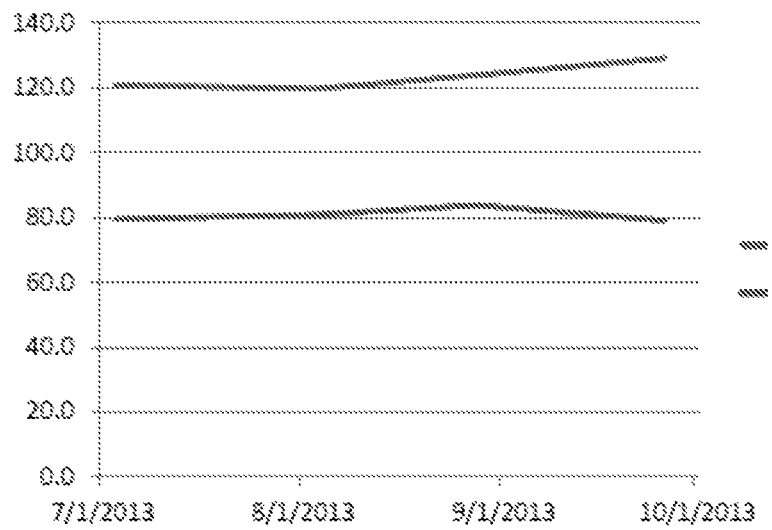
FIG. 7 shows the blood pressure in mmHg during a period of 3 months (FIG. 7*a* control group 2, FIG. 7*b* experimental group 2), upper line: systolic, lower line diastolic.
Figure 7B:
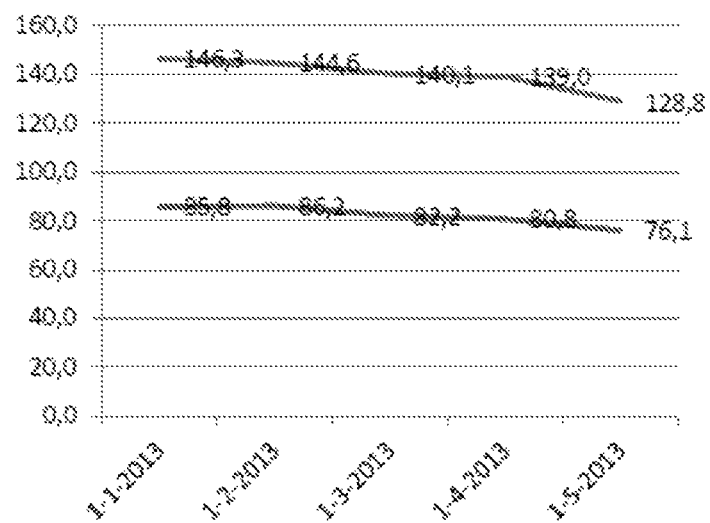

As can be seen in table 1 and in FIGS. 1a and 1b, the reduction of total cholesterol was higher for group 2 than for group 1. Remarkably, the HDL blood levels were increased by using the present medical formulation (group 2) as can be seen in FIGS. 2a and 2b, showing an HDL increase of 5.4 mg/dl. At the same time the present medical formulation provides a stronger reduction in LDL (FIG. 3b) than in group 1 (FIG. 3a). These effects provide a significantly reduced risk factor for the group treated with the medical formulation according to the invention, i.e. a double reduction of 0.99 (group 2, FIG. 5b) in comparison with the reduction of 0.41 for the group 1 (FIG. 5a) treated with lovastatin alone. Accordingly, the ingredients of the medical formulation of the present invention provide a synergistic effect in improving the cholesterol levels in blood. Further, group 2 had improved triglycerides levels as compared with the decrease for group 1. The blood level, as shown in table 1 and FIG. 7, as especially the systolic blood pressure in group 2 was significantly reduced (−35.5) while the systolic blood pressure in group 1 was increased (+10). The lowered systolic blood pressure of the group 2 shows that the present medical formulation improves blood pressure and the viscosity of the blood. The individuals of group 2 did not perceive side effects during the three months trial. Accordingly, the present medical formulation is an advantageous alternative for treating hypercholesterolemia instead of statins.

The invention claimed is:

1. A medical formulation comprising:
   cinnamomum zeylanicum;
   Pinus pinaster;
   extract of a plant belonging to the Saccharum genus;
   Monascus purpureus;
   Taraxacum officinale;
   Camellia sinensis;
   vitamin B3;
   alpha tocopherol;
   coenzyme $Q_{10}$;
   fish oil comprising eicosapentaenoic acid and docosahexanoic acid;
   beta-glucan; and
   cholecalciferol,
   wherein the formulation is an oral, intravenous, subcutaneous, intraperitoneal, topical, parenteral, buccal, nasal, vaginal or rectal formulation in the form of a tablet, a pellet, a capsule, an emulsion, a cream, an ointment, a gel, or a suppository formulation.

2. The medical formulation according to claim 1, comprising:
   bark extract of cinnamomum zeylanicum;
   fibre extract of Pinus pinaster;
   bark extract of a plant belonging to the Saccharum genus;
   extract of Monascus purpureus;
   leaf extract of Taraxacum officinale;
   leaf extract of Camellia sinensis;
   vitamin B3;
   alpha tocopherol;
   coenzyme $Q_{10}$;
   fish oil comprising 15 to 25 wt % of the fish oil eicosapentaenoic acid and 7 to 15 wt % of the fish oil docosahexanoic acid;
   beta-glucan;
   cholecalciferol; and
   zinc bisglycinate.

3. The medical formulation according to claim 1, comprising, as daily dose:
   1 to 500 mg bark extract of cinnamomum zeylanicum;
   1 to 300 mg fibre extract of Pinus pinaster;
   1 to 300 mg bark extract of a plant belonging to the Saccharum genus;
   1 to 1500 mg extract of Monascus purpureus;
   1 to 300 mg leaf extract of Taraxacum officinale;
   1 to 300 mg leaf extract of Camellia sinensis;
   1 to 300 mg vitamin B3;
   1 to 300 mg 50% alpha tocopherol;
   1 to 400 mg coenzyme $Q_{10}$;
   1 to 500 mg fish oil comprising 18 to 22 wt % of the fish oil eicosapentaenoic acid and 10 to 15 wt % of the fish oil docosahexanoic acid;
   0.1 to 150 mg beta-glucan;
   0.1 to 200 mg cholecalciferol; and
   1 to 100 mg zinc bisglycinate.

4. The medical formulation according to claim 1, comprising, as daily dose:
   1 to 50 mg bark extract of cinnamomum zeylanicum;
   1 to 50 mg fibre extract of Pinus pinaster;
   1 to 50 mg bark extract of a plant belonging to the Saccharum genus;
   1 to 150 mg extract of Monascus purpureus;
   0.5 to 50 mg leaf extract of Taraxacum officinale;
   1 to 50 mg leaf extract of Camellia sinensis;
   1 to 50 mg vitamin B3;
   1 to 20 mg 50% alpha tocopherol;
   10 to 150 mg coenzyme $Q_{10}$;
   1 to 150 mg fish oil comprising 15 to 25 wt % of the fish oil eicosapentaenoic acid and 7 to 15 wt % of the fish oil docosahexanoic acid;
   0.5 to 100 mg beta-glucan;
   0.5 to 20 mg cholecalciferol; and
   1 to 50 mg zinc bisglycinate.

5. The medical formulation according to claim 1, further comprising micronutrients and/or trace elements.

6. The medical formulation according to claim 1, further comprising pharmaceutically acceptable carriers and excipients.

7. The medical formulation according to claim 1, formulated for oral administration.

8. A method comprising administering the medical formulation according to claim 1 to a patient.

9. The method according to claim 8, wherein the administering is sufficient for preventing or treating or a combination thereof a disease selected from the group consisting of hypercholesterolemia, atherosclerosis, stroke, hypertension, diabetes mellitus and coronary heart disease in the patient.

10. The method according to claim 8, wherein the administering is sufficient to cause recuperation of vascular walls, lowering low density lipoprotein blood levels, lowering the viscosity of blood, lowering blood pressure, lower risk of thrombosis, preventing hardening of the vessel wall, or increasing high density lipoprotein levels, or a combination thereof, in the patient.

11. The method according to claim 8, wherein the administering is sufficient for preventing or treating, or a combination thereof, a disease selected from the group consisting of hypercholesterolemia, atherosclerosis, stroke, hypertension, thrombosis, diabetes mellitus and coronary heart disease in the patient.

12. The medical formulation according to claim 7, wherein the medical formulation is formulated in a capsule comprising a gelatin.

13. The medical formulation according to claim 1, comprising, as daily dose:
   70 mg bark extract of cinnamomum zeylanicum;
   45 mg fibre extract of Pinus pinaster;
   45 mg bark extract of a plant belonging to the Saccharum genus;
   700 mg extract of Monascus purpureus;
   50 mg leaf extract of Taraxacum officinale;
   100 mg leaf extract of Camellia sinensis;
   20 mg vitamin B3;
   20 mg 50% alpha tocopherol;
   100 mg coenzyme $Q_{10}$;
   155 mg fish oil comprising 19.2 wt % of the fish oil eicosapentaenoic acid and 12.9 wt % of the fish oil docosahexanoic acid;
   1 mg beta-glucan; and
   1 mg cholecalciferol.

14. The medical formulation according to claim 1, comprising, as daily dose:
   4.8 mg bark extract of cinnamomum zeylanicum;
   24.2 mg fibre extract of Pinus pinaster;
   24 mg bark extract of a plant belonging to the Saccharum genus;
   11.4 mg extract of Monascus purpureus;

1.2 mg leaf extract of *Taraxacum officinale*;
16 mg leaf extract of *Camellia sinensis*;
20 mg vitamin B3;
14 mg 50% alpha tocopherol;
60 mg coenzyme $Q_{10}$;
37.8 mg fish oil comprising 19.2 wt % of the fish oil eicosapentaenoic acid and
12.9 wt % of the fish oil docosahexanoic acid;
60 mg beta-glucan; and
1 mg cholecalciferol.

15. The medical formulation according to claim 1, further comprising a capsule comprising a gelatin configured to contain the medical formulation.

* * * * *

UNITED STATES PATENT AND TRADEMARK OFFICE
CERTIFICATE OF CORRECTION

PATENT NO. : 9,655,942 B2
APPLICATION NO. : 14/654270
DATED : May 23, 2017
INVENTOR(S) : Taal It is certified that error appears in the above-identified patent and that said Letters Patent is hereby corrected as shown below:

On the Title Page

At Item (12): Delete "Taal et al." and insert --Taal-- and

At Item (72), Inventors: Delete "Anita Monique Taal-Vals, Hengelo (NL)"

Signed and Sealed this
Fourteenth Day of May, 2019

Andrei Iancu
*Director of the United States Patent and Trademark Office*